(12) United States Patent
Sermet et al.

(10) Patent No.: US 7,896,958 B2
(45) Date of Patent: Mar. 1, 2011

(54) DEVICE FOR SUPPLYING DOMICILIARY AND AMBULATORY OXYGEN

(75) Inventors: Eric Sermet, Hangzhou (CN); Eliette Ferre, Paris (FR); Philippe Dodier, St Foy les Lyon (FR); Joseph Mazoyer, St Foy les Lyon (FR)

(73) Assignee: L'Air Liquide Societe Anonyme pour l'Etude Et l'Exploitation des Procedes Georges Claude, Paris (FR)

( * ) Notice: Subject to any disclaimer, the term of this patent is extended or adjusted under 35 U.S.C. 154(b) by 312 days.

(21) Appl. No.: 12/120,017

(22) Filed: May 13, 2008

(65) Prior Publication Data

US 2009/0020015 A1    Jan. 22, 2009

(30) Foreign Application Priority Data

May 14, 2007    (FR) .................................. 07 55058

(51) Int. Cl.
*B01D 53/02*    (2006.01)
(52) U.S. Cl. ...................... 96/108; 96/130; 128/205.12; 128/205.27
(58) Field of Classification Search ................... 96/108, 96/130; 128/205.12, 205.27; 220/560.04
See application file for complete search history.

(56) References Cited

U.S. PATENT DOCUMENTS

| | | | |
|---|---|---|---|
| 6,346,139 B1 | 2/2002 | Czabala | |
| 6,446,630 B1 | 9/2002 | Todd, Jr. | |
| 7,213,400 B2 | 5/2007 | Dickerson et al. | |
| 7,318,327 B2 | 1/2008 | Dickerson et al. | |
| 7,555,916 B2 | 7/2009 | Dickerson et al. | |
| 2008/0277399 A1* | 11/2008 | Burns et al. | 220/560.04 |

FOREIGN PATENT DOCUMENTS

| | | |
|---|---|---|
| WO | WO 99/11989 | 3/1999 |
| WO | WO 01/33135 | 5/2001 |
| WO | WO 2006 047710 | 5/2006 |
| WO | WO 2007/118054 | 10/2007 |

OTHER PUBLICATIONS

Search Report for FR 0755058, Jan. 10, 2008.
EP Search Report and Written Opinion for co-pending EP 08305116.9.

* cited by examiner

*Primary Examiner*—Robert A Hopkins
(74) *Attorney, Agent, or Firm*—Donna Blalock Holguin

(57) ABSTRACT

Device for supplying domiciliary and ambulatory oxygen, comprising an oxygen filling station and a portable oxygen reserve that can be selectively connected to the filling station, the filling station comprising an oxygen concentrator intended to isolate gaseous oxygen from the air, a liquefier connected to one outlet of the concentrator to receive the isolated gaseous oxygen so that it can be liquefied, a transfer connector connected to one outlet of the liquefier and intended to be connected to an inlet connector of the reserve, the reserve comprising a tank connected to the inlet connector so that liquid oxygen can be transferred from the filling station to the tank, a delivery system comprising members for tapping off, heating and regulating the flow of the oxygen from the tank so as to deliver gaseous oxygen to a patient.

31 Claims, 4 Drawing Sheets

DEVICE FOR SUPPLYING DOMICILIARY AND AMBULATORY OXYGEN

This application claims the benefit of priority under 35 U.S.C. §119 (a) and (b) to French Application No. 0755058, filed May 14, 2007, the entire contents of which are incorporated herein by reference.

BACKGROUND

1. Field of the Invention

The present invention relates to a device for supplying domiciliary and ambulatory oxygen.

2. Related Art

There are numerous ways of offering gaseous oxygen in the context of oxygen therapy treatment. One known option is to provide a reserve of liquid oxygen at the home of the patient and to which the patient is connected when he remains stationed at home, the reserve allowing him to fill a portable tank that the patient can carry with him as he moves around. This solution does, however, present logistic and distribution problems related to the supplying of the reserve of liquid oxygen.

In order to get around this problem with distributing the liquid oxygen, another option is to produce pressurized gaseous oxygen in the home from a concentrator. This solution does, however, require the oxygen to be compressed to a high pressure level, thus increasing the risks to the user. Furthermore, this system generally has low autonomy and because of its weight is ill-suited to moving around.

Another option proposes the use of a portable concentrator. However, this type of system is then dependent on a power supply (battery) and its operation is somewhat unsatisfactory on account, in particular: of its poor robustness, its noisy operation, and its significant weight.

Another proposed solution is to produce liquid oxygen in the patient's home using a concentrator coupled to a liquefier. However, solutions of this type are generally very complicated and ergonomically unsatisfactory (because numerous connection and disconnection operations are needed according to the type of use).

Document WO 99/11989 describes, for example, a fixed oxygen supply device comprising a concentrator, a liquefier and a portable reserve, the patient being connected to the liquefier in his home but connected to the portable reserve when out and about.

SUMMARY OF THE INVENTION

It is one object of the present invention to alleviate all or some of the aforementioned disadvantages of the prior art.

To this end, the device for supplying domiciliary and ambulatory oxygen according to the invention is essentially characterized in that it comprises an oxygen filling station and a portable oxygen reserve that can be selectively connected to the filling station, the filling station comprising an oxygen concentrator intended to isolate gaseous oxygen from the air, a liquefier connected to one outlet of the concentrator to receive the isolated gaseous oxygen so that it can be liquefied, a transfer connector connected to one outlet of the liquefier and intended to be connected to an inlet connector of the reserve, the reserve comprising a tank connected to the inlet connector so that liquid oxygen can be transferred from the filling station to the tank, a delivery system comprising members for tapping off, heating and regulating the flow of the oxygen from the tank so as to deliver gaseous oxygen to a patient, the oxygen supply device comprising a gaseous oxygen outlet connector intended to be connected to the airways of a patient, the said oxygen outlet connector being situated on the portable oxygen reserve downstream of the delivery system, so that the patient can remain constantly connected to the reserve and supplied with gaseous oxygen thereby, that is to say both when the reserve is connected to the filling station and when it is not.

Furthermore, embodiments of the invention may include one or more of the following features:

the device comprises a single gaseous oxygen outlet connector intended to be connected to the airways of a patient, the said single connector being situated on the portable oxygen reserve so that the patient has to remain constantly connected to the reserve in order to be supplied with gaseous oxygen both when the reserve is connected to the filling station and when it is not, the device comprises a member for measuring the level of liquid in the tank of the reserve, the said level measurement member being connected to the filling station to form an automatic feedback control loop controlling the transfer of liquid oxygen from the filling station to the tank, the tank of the reserve comprises a gaseous oxygen outlet connected to the outlet connector via a gas heater and a flow regulating element such as a valve or a flow regulating valve, the device comprises an economizer capable of recirculating the boiled-off gaseous oxygen from the tank to a patient and a safety member such as a relief valve designed to release the boiled-off gaseous oxygen to the outside when the pressure within the tank exceeds a certain threshold and the economizer is not recirculating or not recirculating enough gaseous oxygen to the patient, the economizer and the safety member are positioned between the heater and the flow regulating element, the tank of the reserve comprises a liquid oxygen outlet connected to the outlet connector via a liquid heater and a flow regulating element such as a valve or a flow regulating valve, the tank of the reserve comprises a gaseous oxygen vent outlet that can be connected to the filling station for a possible exchange of heat with the isolated gaseous oxygen with a view to liquefying it, the vent outlet is connected to the liquefier in order to cool a liquefaction immersion tube of the liquefier, the filling station comprises a folding portable housing capable of being connected to a source of electrical power.

BRIEF DESCRIPTION OF THE FIGURES

Other features and advantages will become apparent from reading the description hereinafter which is given with reference to the figures in which.

DETAILED DESCRIPTION OF THE INVENTION

Referring now to the figures, the device for supplying domiciliary and ambulatory oxygen according to the invention comprises an oxygen filling station 1 and a portable oxygen reserve 2.

Figure 1:
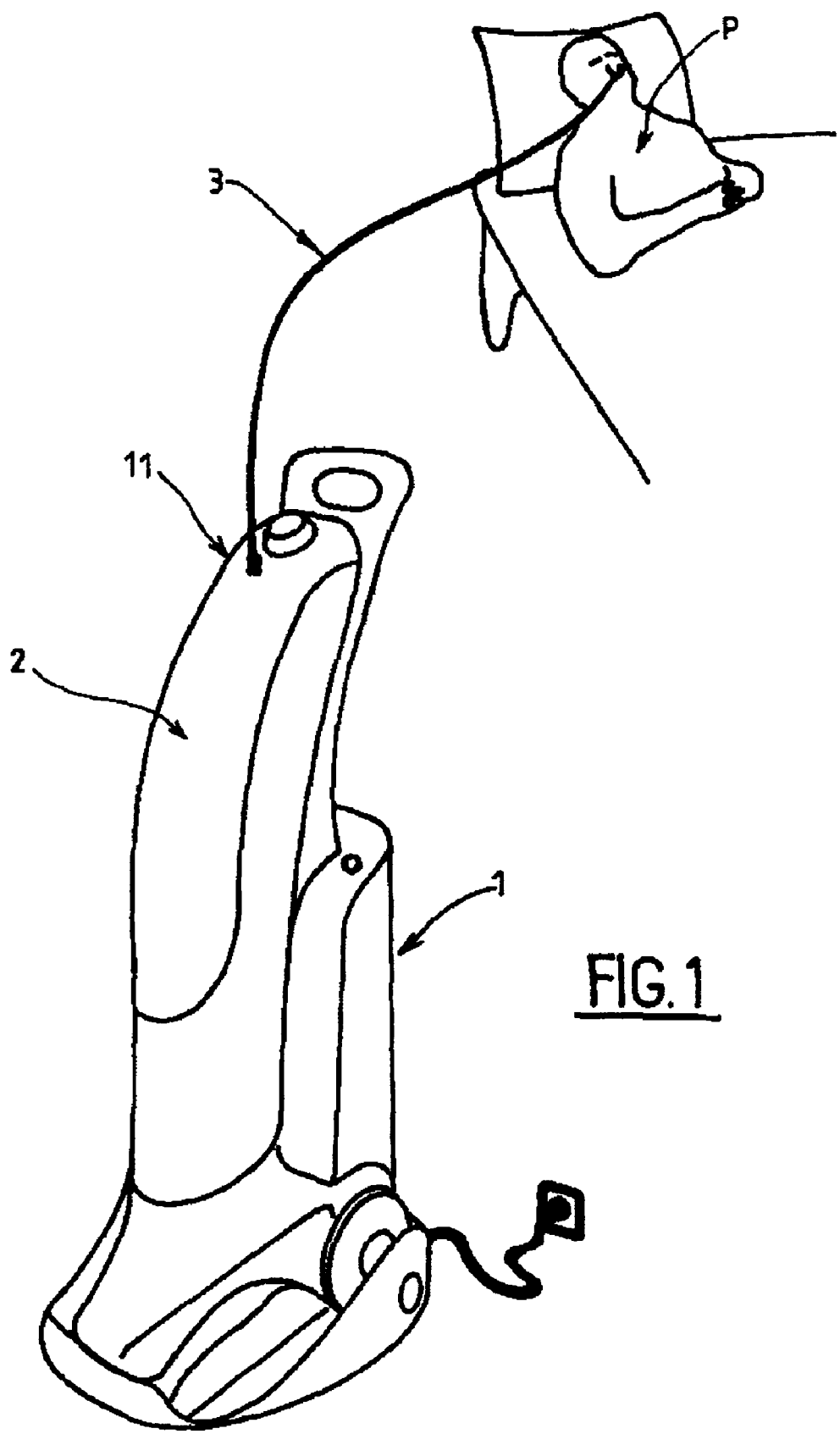
FIG. 1 depicts a schematic view illustrating one example of a device for supplying domiciliary and ambulatory oxygen according to the invention during so-called "fixed" use by a patient (for example for overnight)
Figure 2:
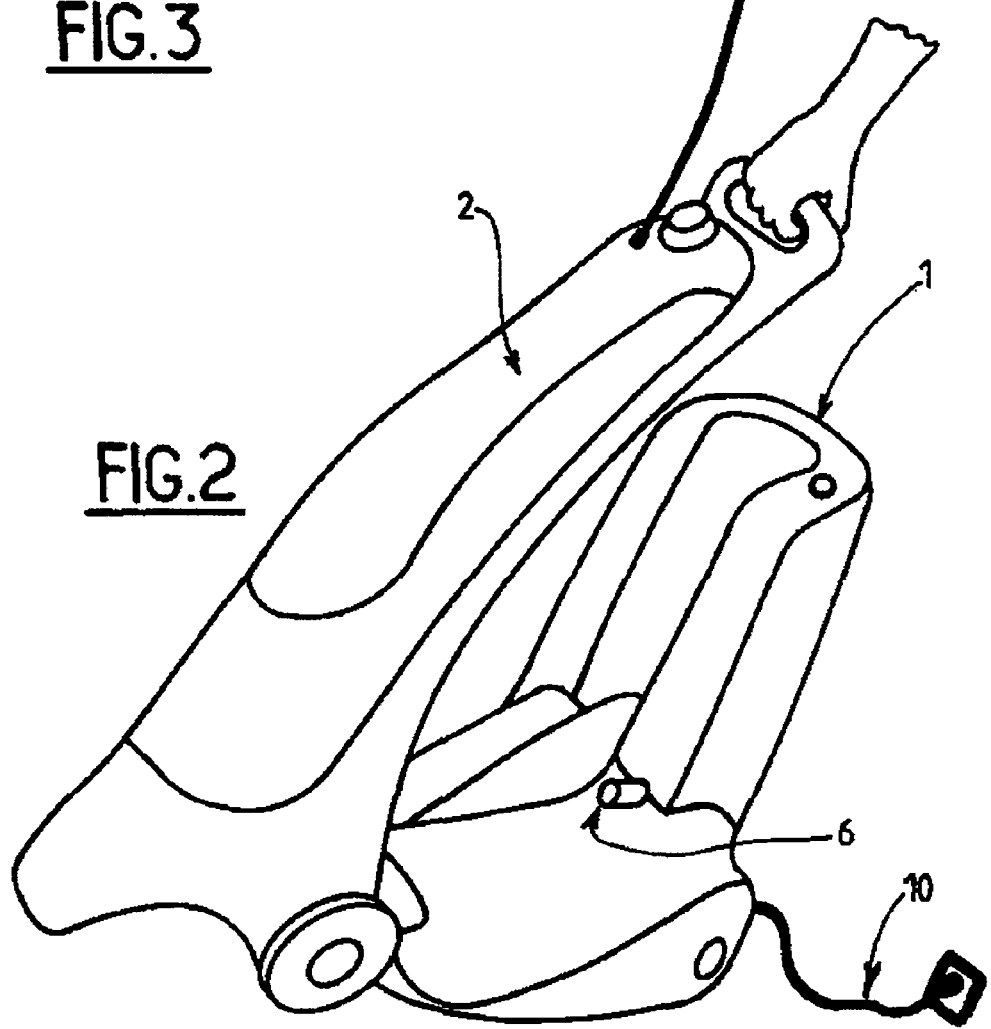
FIG. 2 depicts a schematic and partial view of the device for supplying domiciliary and ambulatory oxygen of FIG. 1 during so-called "mobile" use by a patient (for example during the daytime)
Figure 4:
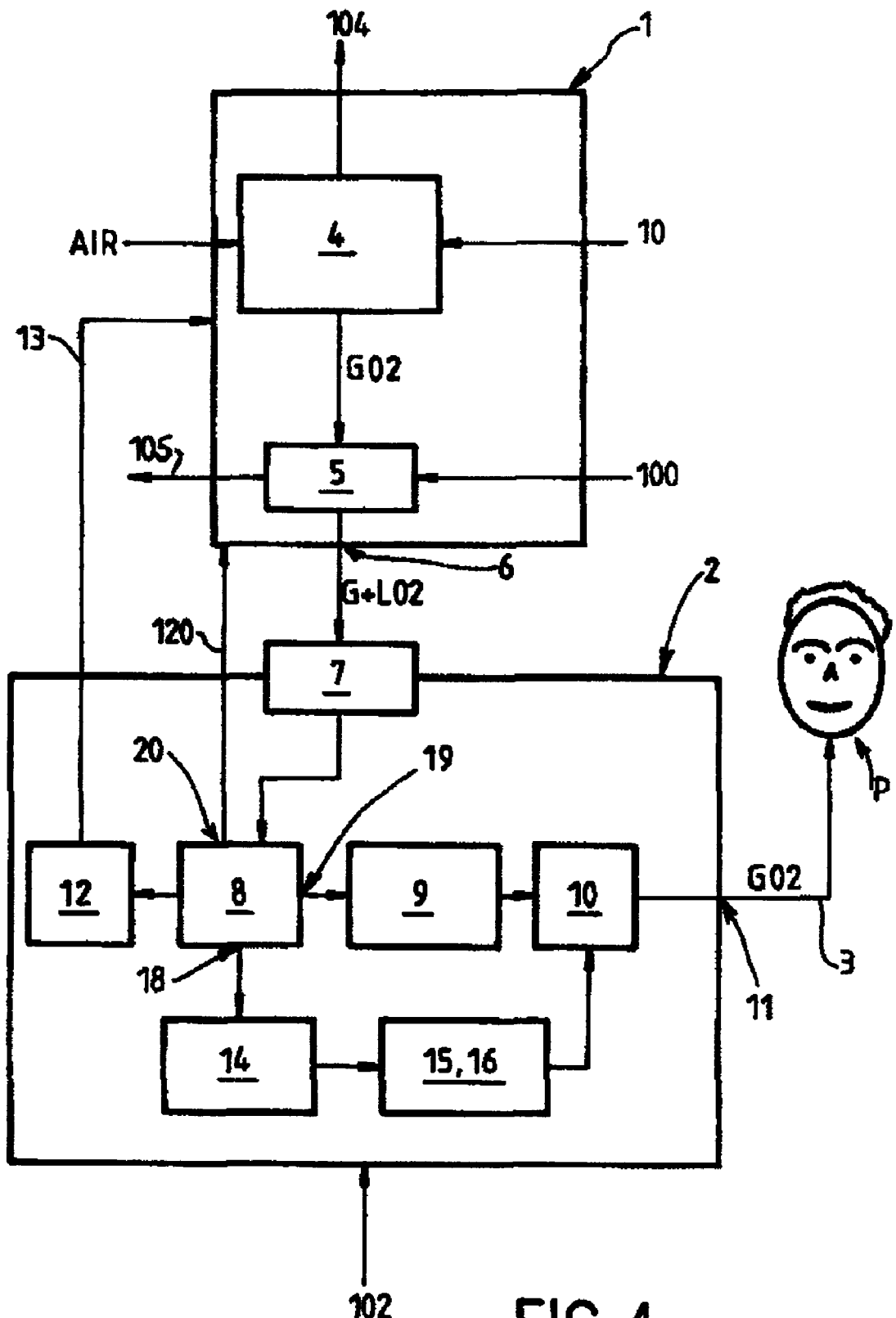
FIG. 4 depicts a schematic view illustrating the structure and operation of the device for supplying domiciliary and ambulatory oxygen according to the invention in fixed use.
Figure 5:
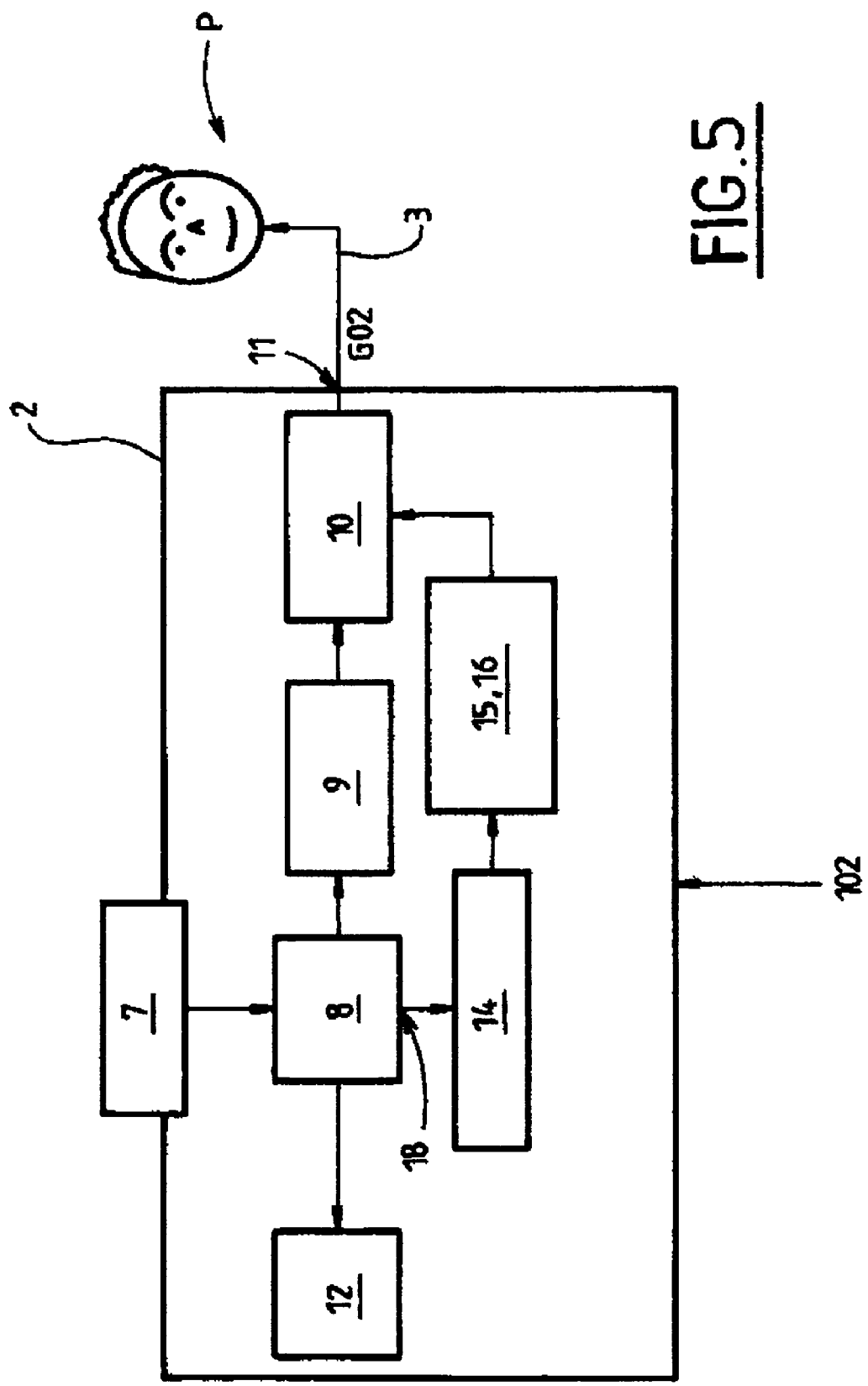
FIG. 5 depicts a schematic view illustrating the structure and operation of part of the device of FIG. 4 during mobile use.

The portable oxygen reserve 2 can be selectively connected (FIGS. 1 and 4) to the filling station 1 or disconnected from the filling station 1 (FIGS. 2 and 5).

With reference more precisely now to FIG. 4, the filling station 1 comprises an oxygen concentrator 4 intended to isolate gaseous oxygen from the air and a liquefier 5 connected to one outlet of the concentrator 4 to receive the isolated gaseous oxygen GO2 so that it can be liquefied.

The oxygen concentrator 4 may comprise a system of the pressure swing adsorption (PSA) or equivalent type.

Conventionally, and as symbolized in FIG. 4, the oxygen concentrator 4 is supplied with air and with power (such as mains electricity) and produces heat 104.

The liquefier 5, for example of the STIRLING cooler type, or a pulse gas tube cooler, is supplied with oxygen-enriched gas by the concentrator GO2, with power 100 (for example mains electricity) and generates heat 105 as the oxygen is liquefied.

The liquefier 5 produces a mixture of liquid and gaseous oxygen G+L O2.

On the outlet side, the filling station 1 comprises a transfer connector 6 connected to the oxygen outlet of the liquefier 5 (FIGS. 2 and 4) and intended to be connected to an inlet connector 7 of the reserve 2.

The reserve 2 comprises a cryogenic tank 8 connected to the inlet connector 7 so that liquid oxygen can be transferred from the filling station 1 into the tank 8.

Conventionally, the reserve 2 comprises a gaseous oxygen delivery system 9, 10 comprising components for tapping off, heating and regulating the flow of the oxygen from the tank 8 so that it can be administered to a patient P.

Conventionally, the delivery system may comprise a liquid heater member 9 (for example a heat exchange coil to exchange heat with the external air 102) and flow regulating members 10 (such as at least one valve, preferably of variable and adjustable flow rate).

In order to supply a patient P with gaseous oxygen, the reserve 2 comprises a gaseous oxygen outlet connector 11 intended to be connected 3 (for example via oxygen spectacles or an oxygen mask) to the airways of a patient P.

According to one particularly advantageous special feature, the patient P can remain constantly connected to the reserve 2 and supplied with gaseous oxygen thereby, that is to say both when the reserve 2 is connected to the filling station 1 and when the reserve 2 is not connected to the filling station 1.

To achieve this, the device may comprise a single gaseous oxygen outlet connector 11 situated on the portable oxygen reserve 2 so that the patient P has to remain constantly connected to the reserve 2 in order to be supplied with gaseous oxygen (during the daytime: FIGS. 2 and 5, and during the night-time: FIGS. 1 and 4).

As a preference, the device comprises a sensor 12 for measuring the liquid level in the tank 8 of the reserve 2. The measurement information from this level sensor 12 is transmitted to the filling station 1 to form an automatic feedback control loop 13 controlling the transfer of liquid oxygen from the filling station 1 to the tank 8. What that means is that when the reserve 2 is connected to the filling station 1, depending on the measurement of the level of liquid in the tank 8, the station will either supply the reserve with liquid oxygen or not, depending on whether the level in the tank 8 is below or above a threshold value.

Furthermore, the tank 8 of the reserve 2 comprises a vent outlet 20 for gaseous oxygen. According to one advantageous special feature, a pipe 120 allows this cold vent gas to be placed in a heat exchange relationship with the isolated gaseous oxygen in the filling station 1 so as to liquefy it.

For example, the vent gas may be carried by the pipe 120 to the liquefier 5 in order, for example, to cool a refrigerating immersion tube belonging to the liquefier 5.

The tank 8 of the reserve 2 further comprises an outlet 18 for gaseous oxygen (for example the boil-off oxygen) which is connected to the outlet connector 11 via a gas heater 14 and a flow regulating element 10 such as at least one valve or flow regulating valve.

In the conventional way, the gas heater 14 may comprise a heat exchanger such as a coil in a heat exchange relationship with the external air 102.

An economizer 15 capable of recirculating the boiled-off gaseous oxygen from the tank 8 to the patient is positioned downstream of the gas heater 14.

The economizer 15 provides automatic pressure regulation of the pressure in the tank 8 by diverting excess gas from the tank 8 to the patient P (via the regulating element 10). When the patient P is not connected (regulating element 10 closed) and/or in the event of a dangerous overpressure, the gas is discharged by a safety member 16 such as a relief valve described in greater detail hereinbelow.

Upstream or downstream of the economizer 15 there is a safety member 16 such as a relief valve designed to release boil-off gaseous oxygen to the outside when the pressure in the tank 8 and/or in the circuit exceeds a determined threshold.

Thus, any excess gaseous oxygen in the tank 8 is recirculated to the patient P instead of being lost to the atmosphere. The oxygen consumption of the system is thus better controlled.

Figure 3:
FIG. 3 depicts a schematic and partial view of part of the device of FIGS. 1 and 2 in a handling position (folding and transporting the oxygen production base of the device)

As depicted in FIGS. 1 to 3, the filling station 1 preferably comprises a base that can be folded for handling (FIG. 3).

Likewise, the reserve 2 may be built into a housing mounted on wheels and comprising a handgrip at the top for grasping.

The invention displays numerous advantages.

The single oxygen outlet connector 11 allows the use of a single liquid oxygen tank 8, a single regulating valve for regulating the flow delivered to the patient . . . (and ditto for the other fluid regulating components in the circuit on the outlet side of the tank).

In addition, according to the invention, the patient is always supplied with gaseous oxygen from the liquid oxygen of the single tank 8.

This improves the purity of the oxygen delivered (by comparison with oxygen supplied directly from the outlet side of a gas concentrator).

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A device for supplying domiciliary and ambulatory oxygen, comprising an oxygen filling station and a portable oxygen reserve that can be selectively connected to the filling station, the filling station comprising an oxygen concentrator intended to isolate gaseous oxygen from the air, a liquefier connected to one outlet of the concentrator to receive the isolated gaseous oxygen so that it can be liquefied, a transfer connector connected to one outlet of the liquefier and intended to be connected to an inlet connector of the reserve and a folding portable housing capable of being connected to a source of electrical power, the reserve comprising a tank connected to the inlet connector so that liquid oxygen can be transferred from the filling station to the tank, a delivery system comprising members for tapping off, heating and regulating the flow of the oxygen from the tank so as to deliver gaseous oxygen to a patient, the oxygen supply device comprising a gaseous oxygen outlet connector intended to be connected to the airways of a patient, the said oxygen outlet connector being situated on the portable oxygen reserve downstream of the delivery system, the device having a single gaseous oxygen outlet connector intended to be connected to the airways of a patient, the said single connector being situated on the portable oxygen reserve so that the patient has to remain constantly connected to the reserve in order to be supplied with gaseous oxygen by the latter both when the reserve is connected to the filling station and when it is not.

2. The device of claim 1, wherein the tank of the reserve constitutes the only liquid oxygen storage tank of the device, and in that the patient is supplied with oxygen solely from the single tank of the reserve via the single connector both when the reserve is connected to the filling station and when it is not.

3. The device of claim 1, wherein the device further comprises a member for measuring the level of liquid in the tank of the reserve, the said level measurement member being connected to the filling station to form an automatic feedback control loop controlling the transfer of liquid oxygen from the filling station to the tank.

4. The device of claim 1, wherein the tank of the reserve comprises a gaseous oxygen outlet connected to the outlet connector via a gas heater and a flow regulating element such as a valve or a flow regulating valve.

5. The device of claim 4, wherein the device further comprises an economizer capable of recirculating the boiled-off gaseous oxygen from the tank to a patient and a safety member such as a relief valve designed to release the boiled-off gaseous oxygen to the outside when the pressure within the tank exceeds a certain threshold and the economizer is not recirculating or not recirculating enough gaseous oxygen to the patient.

6. The device of claim 5, wherein the economizer and the safety member are positioned between the heater and the flow regulating element.

7. The device of claim 1, wherein the tank of the reserve comprises a liquid oxygen outlet connected to the outlet connector via a liquid heater and a flow regulating element such as a valve or a flow regulating valve.

8. The device of claim 1, wherein the tank of the reserve comprises a gaseous oxygen vent outlet that can be connected to the filling station for a possible exchange of heat with the isolated gaseous oxygen with a view to liquefying it.

9. The device of claim 8, wherein the vent outlet is connected to the liquefier in order to cool a liquefaction immersion tube of the liquefier.

10. The device of claim 2, wherein the device further comprises a member for measuring the level of liquid in the tank of the reserve, the said level measurement member being connected to the filling station to form an automatic feedback control loop controlling the transfer of liquid oxygen from the filling station to the tank.

11. The device of claim 10, wherein the tank of the reserve comprises a gaseous oxygen outlet connected to the outlet connector via a gas heater and a flow regulating element such as a valve or a flow regulating valve.

12. The device of claim 11, wherein the device further comprises an economizer capable of recirculating the boiled-off gaseous oxygen from the tank to a patient and a safety member such as a relief valve designed to release the boiled-off gaseous oxygen to the outside when the pressure within the tank exceeds a certain threshold and the economizer is not recirculating or not recirculating enough gaseous oxygen to the patient.

13. The device of claim 12, wherein the economizer and the safety member are positioned between the heater and the flow regulating element.

14. The device of claim 13, wherein the tank of the reserve comprises a liquid oxygen outlet connected to the outlet connector via a liquid heater and a flow regulating element such as a valve or a flow regulating valve.

15. The device of claim 14, wherein the tank of the reserve comprises a gaseous oxygen vent outlet that can be connected to the filling station for a possible exchange of heat with the isolated gaseous oxygen with a view to liquefying it.

16. The device of claim 15, wherein the vent outlet is connected to the liquefier in order to cool a liquefaction immersion tube of the liquefier.

17. The device of claim 16, wherein the filling station comprises a folding portable housing capable of being connected to a source of electrical power.

18. A device for supplying domiciliary and ambulatory oxygen, comprising an oxygen filling station and a portable oxygen reserve that can be selectively connected to the filling station, the filling station comprising an oxygen concentrator intended to isolate gaseous oxygen from the air, a liquefier connected to one outlet of the concentrator to receive the isolated gaseous oxygen so that it can be liquefied, a transfer connector connected to one outlet of the liquefier and intended to be connected to an inlet connector of the reserve, the reserve comprising a tank connected to the inlet connector so that liquid oxygen can be transferred from the filling station to the tank, the tank comprising a gaseous oxygen outlet connected to the outlet connector via a gas heater and a flow regulating element, a delivery system comprising members for tapping off, heating and regulating the flow of the oxygen from the tank so as to deliver gaseous oxygen to a patient, the oxygen supply device comprising a gaseous oxygen outlet connector intended to be connected to the airways of a patient, the said oxygen outlet connector being situated on the portable oxygen reserve downstream of the delivery system, and an economizer capable of recirculating the boiled-off gaseous oxygen from the tank to a patient and a safety member such as a relief valve designed to release the boiled-off gaseous oxygen to the outside when the pressure within the tank exceeds a certain threshold and the economizer is not recirculating or not recirculating enough gaseous oxygen to the patient, the device having a single gaseous oxygen outlet connector intended to be connected to the airways of a patient, the said single connector being situated on the portable oxygen reserve so that the patient has to remain constantly connected to the reserve in order to be supplied with gaseous oxygen by the latter both when the reserve is connected to the filling station and when it is not.

19. The device of claim 18, wherein the tank of the reserve constitutes the only liquid oxygen storage tank of the device, and in that the patient is supplied with oxygen solely from the single tank of the reserve via the single connector both when the reserve is connected to the filling station and when it is not.

20. The device of claim 18, wherein the device further comprises a member for measuring the level of liquid in the tank of the reserve, the said level measurement member being connected to the filling station to form an automatic feedback control loop controlling the transfer of liquid oxygen from the filling station to the tank.

21. The device of claim 18, wherein the flow regulating element is a valve or a flow regulating valve.

22. The device of claim 18, wherein the economizer and the safety member are positioned between the heater and the flow regulating element.

23. The device of claim 18, wherein the tank of the reserve comprises a liquid oxygen outlet connected to the outlet connector via a liquid heater and a flow regulating element such as a valve or a flow regulating valve.

24. The device of claim 18, wherein the tank of the reserve comprises a gaseous oxygen vent outlet that can be connected to the filling station for a possible exchange of heat with the isolated gaseous oxygen with a view to liquefying it.

25. The device of claim 24, wherein the vent outlet is connected to the liquefier in order to cool a liquefaction immersion tube of the liquefier.

26. The device of claim 18, wherein the filling station comprises a folding portable housing capable of being connected to a source of electrical power.

27. The device of claim 19, wherein the device further comprises a member for measuring the level of liquid in the tank of the reserve, the said level measurement member being connected to the filling station to form an automatic feedback control loop controlling the transfer of liquid oxygen from the filling station to the tank.

28. The device of claim 22, wherein the tank of the reserve comprises a liquid oxygen outlet connected to the outlet connector via a liquid heater and a flow regulating element such as a valve or a flow regulating valve.

29. The device of claim 28, wherein the tank of the reserve comprises a gaseous oxygen vent outlet that can be connected to the filling station for a possible exchange of heat with the isolated gaseous oxygen with a view to liquefying it.

30. The device of claim 29, wherein the vent outlet is connected to the liquefier in order to cool a liquefaction immersion tube of the liquefier.

31. The device of claim 30, wherein the filling station comprises a folding portable housing capable of being connected to a source of electrical power.

* * * * *